(12) United States Patent
Wessman

(10) Patent No.: US 7,039,470 B1
(45) Date of Patent: May 2, 2006

(54) MEDICAL LEAD AND METHOD FOR MEDICAL LEAD MANUFACTURE

(75) Inventor: Bradley J. Wessman, Maple Grove, MN (US)

(73) Assignee: MicroNet Medical, Inc., White Bear Lake, MN (US)

( * ) Notice: Subject to any disclaimer, the term of this patent is extended or adjusted under 35 U.S.C. 154(b) by 0 days.

(21) Appl. No.: 09/670,062

(22) Filed: Sep. 26, 2000

(51) Int. Cl.
*A61N 1/06* (2006.01)
(52) U.S. Cl. ..................................... 607/122
(58) Field of Classification Search ................. 29/825, 29/854, 857, 862, 865, 866, 874, 876, 884; 600/373, 377, 393, 395; 607/116–119, 122
See application file for complete search history.

(56) References Cited

U.S. PATENT DOCUMENTS

| | | | |
|---|---|---|---|
| 4,280,511 A * | 7/1981 | O'Neill | 128/784 |
| 4,355,646 A | 10/1982 | Kallok et al. | |
| 4,381,014 A * | 4/1983 | Sandstrom et al. | 128/786 |
| 4,432,377 A | 2/1984 | Dickhudt | 128/786 |
| 4,437,474 A | 3/1984 | Peers-Trevarton | |
| 4,444,195 A | 4/1984 | Gold | |
| 4,559,951 A | 12/1985 | Dahl et al. | |
| 4,566,467 A | 1/1986 | DeHaan | 128/784 |
| 4,590,950 A | 5/1986 | Iwaszkiewicz et al. | 128/786 |
| 4,592,372 A | 6/1986 | Beranek | 128/786 |
| 4,614,395 A | 9/1986 | Peers-Trevarton | 339/97 |
| 4,706,682 A | 11/1987 | Stypulkowski et al. | 128/642 |
| 4,764,324 A | 8/1988 | Burnham | |
| 4,848,352 A | 7/1989 | Pohndorf et al. | |
| 4,890,623 A | 1/1990 | Cook et al. | |
| 4,934,049 A * | 6/1990 | Kiekhafer et al. | 29/883 |
| 4,944,088 A | 7/1990 | Doan et al. | 29/858 |
| 5,016,646 A | 5/1991 | Gotthardt et al. | 128/784 |
| 5,040,544 A | 8/1991 | Lessar et al. | |
| 5,118,400 A | 6/1992 | Wollam | |
| 5,178,957 A | 1/1993 | Kolpe et al. | |
| 5,251,643 A | 10/1993 | Osypka | |
| 5,324,322 A | 6/1994 | Grill, Jr. et al. | |
| 5,374,285 A | 12/1994 | Vaiani et al. | |
| 5,417,208 A * | 5/1995 | Winkler | 128/642 |
| 5,431,681 A | 7/1995 | Helland | 607/4 |
| 5,433,742 A | 7/1995 | Willis | |
| 5,458,629 A * | 10/1995 | Baudino et al. | 607/116 |
| 5,582,609 A | 12/1996 | Swanson et al. | |
| 5,609,622 A | 3/1997 | Soukup et al. | 607/122 |
| 5,712,462 A | 1/1998 | Berkowitz et al. | |
| 5,762,631 A * | 6/1998 | Klein | 604/171 |
| 5,788,692 A | 8/1998 | Campbell et al. | |
| 5,796,044 A | 8/1998 | Cobian et al. | |
| RE35,924 E | 10/1998 | Winkler | 292/348 |

(Continued)

Primary Examiner—Robert E. Pezzuto
Assistant Examiner—Frances P. Oropeza
(74) Attorney, Agent, or Firm—Peter R. Lando

(57) ABSTRACT

A lead employing a connection between a conductor and an electric element is provided. The connection includes a conductive pad electrically connected to at least one conductor and the electric element electrically connected to the conductive pad. The conductive pad can further include an elongated element to connect the pad to the electric element. The method for connecting a conductor to an electric element is also provided. The method includes forming a groove in the insulator of a lead body to expose the conductor. Placing a conductive pad within the groove and electrically connecting a conductive pad to the conductor. An electric element is then placed over the conductive pad and the electric element is electrically connected to the conductive pad.

8 Claims, 6 Drawing Sheets

U.S. PATENT DOCUMENTS

| | | |
|---|---|---|
| 5,928,277 A | 7/1999 | Laske et al. |
| 6,018,684 A | 1/2000 | Bartig et al. |
| 6,151,520 A | 11/2000 | Combs |
| 6,208,881 B1 | 3/2001 | Champeau |
| 6,253,111 B1 * | 6/2001 | Carner ...................... 607/122 |
| 6,324,415 B1 * | 11/2001 | Spehr et al. ................ 600/374 |

* cited by examiner

MEDICAL LEAD AND METHOD FOR MEDICAL LEAD MANUFACTURE

BACKGROUND OF THE INVENTION

1. Field of the Invention

The present invention relates to a medical leads and particularly to a method of medical lead manufacture and medical leads having a conductive pad connecting a band electrode to a conductor.

2. Description of the Related Art

Implantable leads form an electrical connection between a pulse generator or other electronic device and a tissue or structure in the body. For example, leads transmit electric signals used to stimulate cardiac or nerve tissue in one direction and signals generated by sensors placed in proximity to particular organs or tissues in the opposite direction. Leads typically include one or more electrodes at the lead's distal end. The electrodes are designed to form an electrical connection with a tissue or organ. Most leads also include a lead connector at the lead's proximal end. Lead connectors are adapted to electrically and mechanically connect leads to the pulse generators or other electronic medical devices. A conductor connects the electrode to the lead connector. Commonly, the conductor takes the form of a single or multifilar wire coil. Although, there is an increasing interest in using stranded cables as conductors. Regardless of the conductor's form, an insulating material typically surrounds the conductors. Spinal chord stimulation leads are typically formed with individually insulated conductors surrounded by a separate lead body tube. Together, the conductor and the insulating material form the lead body. The lead body couples the lead connector at the proximal end with the electrode at the distal end.

Manufacturing leads is costly. A significant portion of the cost is allocated to electrically connecting the conductors to the various electrodes, sensors and connectors used in the industry. Forming a secure electrical junction has proven difficult and time consuming. Laser welds are commonly used to connect the conductors to the electrodes. The conductors are typically helically wound into a coil for increased reliability and flexibility. Band electrodes are typically connected to conductors by welding in an operation separate from the application of the lead body tube. Once the band electrodes are connected to the conductors, an extruded tube is placed over the conductor coil and welded band electrodes are connected to the lead body tube by insert molding or RF welding. Band electrodes may also be connected to a conductor by etching away a region of insulator, applying a coating of electrically conductive adhesive, and then placing the band electrode around the conductor. This etching method is complex, not amenable to automation and expensive. Therefore, a need exists for a method that reduces complexity and is easily automated to reduce production costs.

In another method of attachment, band electrodes are electrically connected to coiled conductors by placing a soft metal in a hole cut into an insulating sleeve. An electrode is placed over the metal and crimped or swaged to bring the electrode, soft metal and coiled conductors into electrical contact and to secure the electrode to the lead body. The crimping or swaging method of connection results in electrical connections between the conductor and the band electrode that may fail. Further, swaging to electrically connect an electrode to a conductor is time consuming and difficult to implement with the modern reduced diameter leads. Hence, a need exists for an improved manufacturing technique to secure band electrodes to conductors that reduces the time, complexity and cost while increasing reliability.

In addition, current manufacturing techniques frequently require adding elements, such as collars, when connecting a band electrode to a coil. The added elements increase the lead's diameter near the weld. In application, a uniform diameter weld would result in a smaller lead. A smaller diameter lead is desired to allow placement in restricted spaces such as the epidural space or cardiac veins to reduce the effects of implanted lead on the patient. Further, a smaller lead allows for a smaller introducer that reduces the trauma associated with implantation and similarly a smaller removal sheath when explanting the lead. Hence, there exists a need to reduce the diameter of the welds used to secure electrodes to conductors in implantable medical leads.

The present invention meets these needs and provides other advantages and improvements that will be evident to those skilled in the art.

SUMMARY OF THE INVENTION

The present invention provides a lead and method for lead construction that reduces the time, complexity and costs of producing implantable electrical leads by providing a novel connection between the conductors and an electrode, connector or sensor.

The medical lead includes a lead body, a conductive pad and a band. The lead body is comprised of an insulator and at least one conductor. The insulator includes at least one welding region exposing at least one conductor. The welding region may be in the form of a groove cut in the insulator. When in the form of a groove, the welding region typically is cut parallel to the orientation of the conductor. The conductive pad is secured within the welding region to electrically connected to the conductor to the pad. The conductive pad may be composed of stainless steel, MP35N, platinum, gold, silver, copper, vanadium or other metal. The conductive pad may be electrically connected to the conductor by welding, conductive adhesives, crimping or other methods. Alternative to the conductive pad, an elongated conductive element may be used to electrically connected to the conductor to the pad. The elongated conductive element can be a wire, a ribbon wire, a cable, or other elongated form. The elongated conductive element may be composed of stainless steel, MP35N, platinum, gold, silver, copper, vanadium or other metal. The elongated conductive element may be electrically connected to the conductor by welding, conductive adhesives, crimping or other methods. The band is welded to the conductive pad to electrically connect the band to the conductor. The band may be a band electrode, a band connector, a sensor, or other element electrically secured to medical leads. The band may include a plurality of projections on an inner wall of a lumen. The projections space the inner wall from an outer surface of the lead body. Three or more projections may be positioned around the inner wall to center the lead body within the lumen during assembly.

The method for manufacturing a medical lead includes forming a welding region, securing a conductive pad within the welding region, and securing a band to the conductive pad. The welding region is typically formed by cutting through the insulator to expose the conductor. The welding region can cut with a laser, typically an excimer laser, or can be mechanically cut. The conductive pad is secured within the welding region adjacent the conductor. The conductive pad can be secured within the welding region using a weld, crimping conductive adhesives or other method. The band is secured to the conductive pad to electrically connect the band to the conductor. To secure the band, a weld is formed between the conductive pad and the band. A yttrium-arsenic-garnet laser may be used to form the weld.

Alternatively to the use of a conductive band, an elongated conductive element may be substituted. The proximal end of the elongated conductive element is secured conductor within the welding region. The band is then positioned around the lead body and over the welding region. The distal end of the elongated conductive element is then electrically connected to the band. The elongated conductive element may be electrically connected to the band by welding.

DETAILED DESCRIPTION OF THE INVENTION

Figure 1:
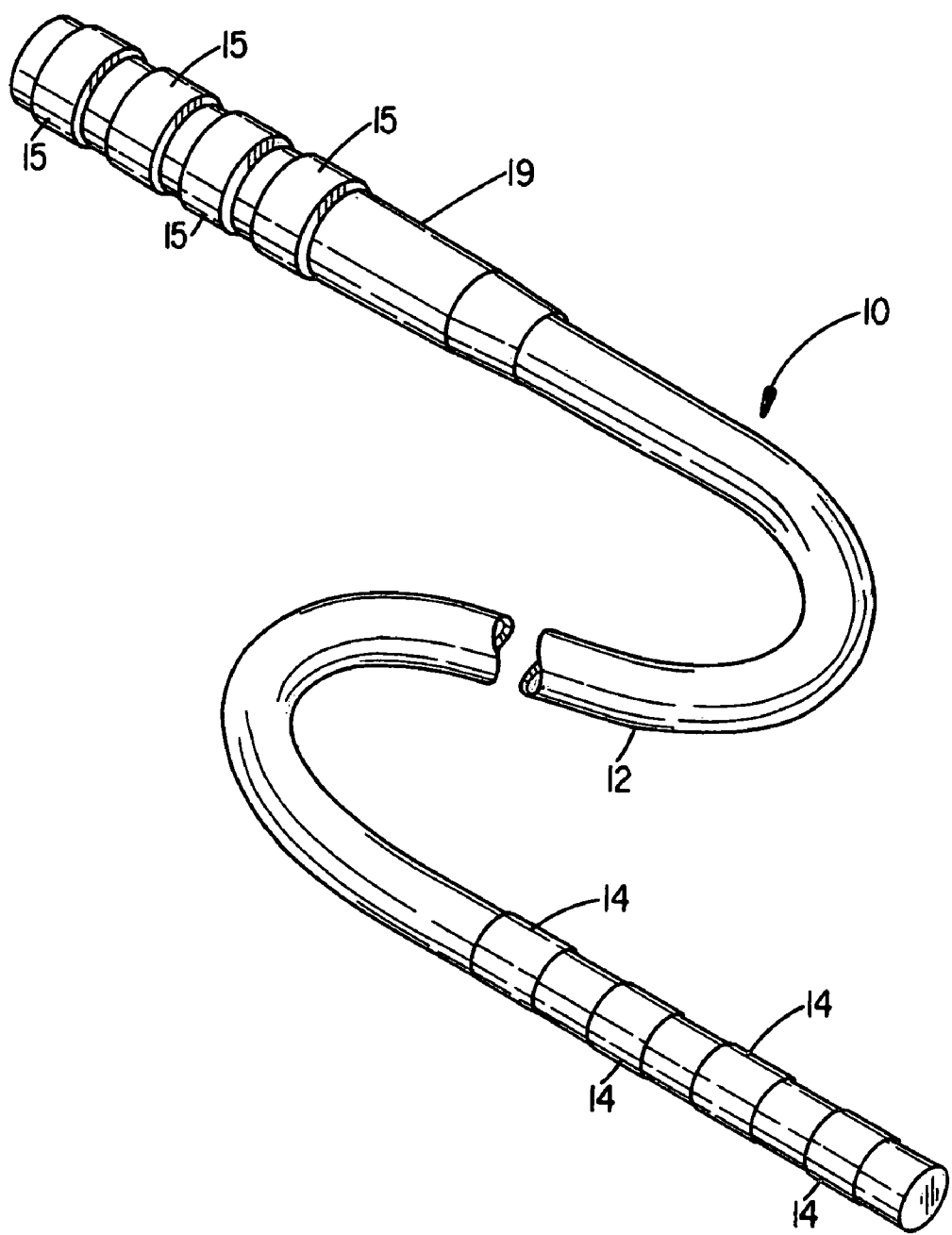
FIG. 1 illustrates a perspective view of a lead in accordance with the present invention.

The present invention provides a medical lead and a method for lead manufacture. The invention is described generally in the context of an electrode for a neurostimulating lead and a method for manufacturing a neurostimulating lead as a specific example for illustrative purposes only. The appended claims are not intended to be limited to any specific example or embodiment described in this patent. It will be understood by those skilled in the art that leads in accordance with the present invention may be used for a wide variety of applications including, but not limited to, leads and catheters for use with cardiac monitoring devices, cardiac rhythm management devices, ablation devices, mapping devices, neurostimulating devices, neuromonitoring devices or other medical devices using leads or catheters. Further, in the drawings described below, the reference numerals are generally repeated where identical elements appear in more than one figure.

FIG. 1 illustrates an embodiment of a lead 10 made in accordance with the present invention. Leads designed for neurostimulation typically have two or more longitudinally spaced band electrodes at the lead's distal end. Lead 10, as shown, includes a lead body 12 and four band electrodes 14. Lead 10 is generally configured to transmit an electric signal from a pulse generator (not shown) to a spinal nerve or peripheral nerve. Thus, electrodes 14 are typically located at the distal end of lead 10. Lead body 12 includes a flexible lead insulator surrounding one or more conductors. The conductors are electrically coupled to the band electrodes. In addition, a lead connector 15 is typically located at the proximal end of lead body 12 to electrically couple the conductors to the pulse generator.

Typically, lead body 12 is a flexible, elastomeric structure having a round cross-section. Alternatively, lead body's cross-section could be any number of shapes appropriate for the specific application. The figures and the following description generally refer to round cross-sectional shape for lead bodies for exemplary purposes. The lead insulator is generally configured to insulate the conductors and to present a smooth biocompatible external surface to body tissues. Thus, the lead insulator is typically coextensive with the conductor or conductors. When a plurality of conductors form a multipolar lead, individual conductors are typically electrically isolated from one another. The insulator material is typically selected based on biocompatibility, biostability and durability for the particular application. The insulator material may be silicone, polyurethane, polyethylene, polyimide, polyvinylchloride, PTFE, ETFE, or other materials known to those skilled in the art. Moreover, alloys and blends of these materials may also be formulated to control the relative flexibility, torqueability, and pushability of the lead. Depending on the particular application, the diameter of the lead body may be as small as 2 French or smaller for neurological and myocardial mapping/ablation leads and can be sizes larger than 12 French for other applications.

The conductors may take the form of solid wires, drawn-filled-tube (DFT), drawn-brazed-strand (DBS), stranded cables or other forms that will be recognized by those skilled in the art. The conductors may be composed of stainless steel, MP35N, or other conductive materials known to those skilled in the art. The number, size, and composition of the conductors will depend on particular application for the lead.

At least one band electrode 14 is positioned at the distal end of lead body 12 for electrically engaging a target tissue or organ. In addition, at least one band connector 15 is positioned at the proximal end of the lead body for electrically connecting the conductors to the neurostimulator. For purposes of the present invention, band electrodes 14 and band connectors 15 are collectively referred to as bands. The bands are typically made of a conductive material such as platinum, gold, silver, platinum-iridium, stainless steel, MP35N or other conductive metals or alloys thereof known to those skilled in the art. The bands are typically composed of a material thin enough to allow for welding of the elements to the underlying conductive pad, as discussed below. For neurostimulation, band electrodes 14 are typically between 1 and 10 millimeters long and have a diameter between about 2 and about 8 French but are more typically between 4 and 6 French. Typically, band connectors 15 have a size and configuration appropriate to connect the lead to a particular neurostimulator.

Figure 2:
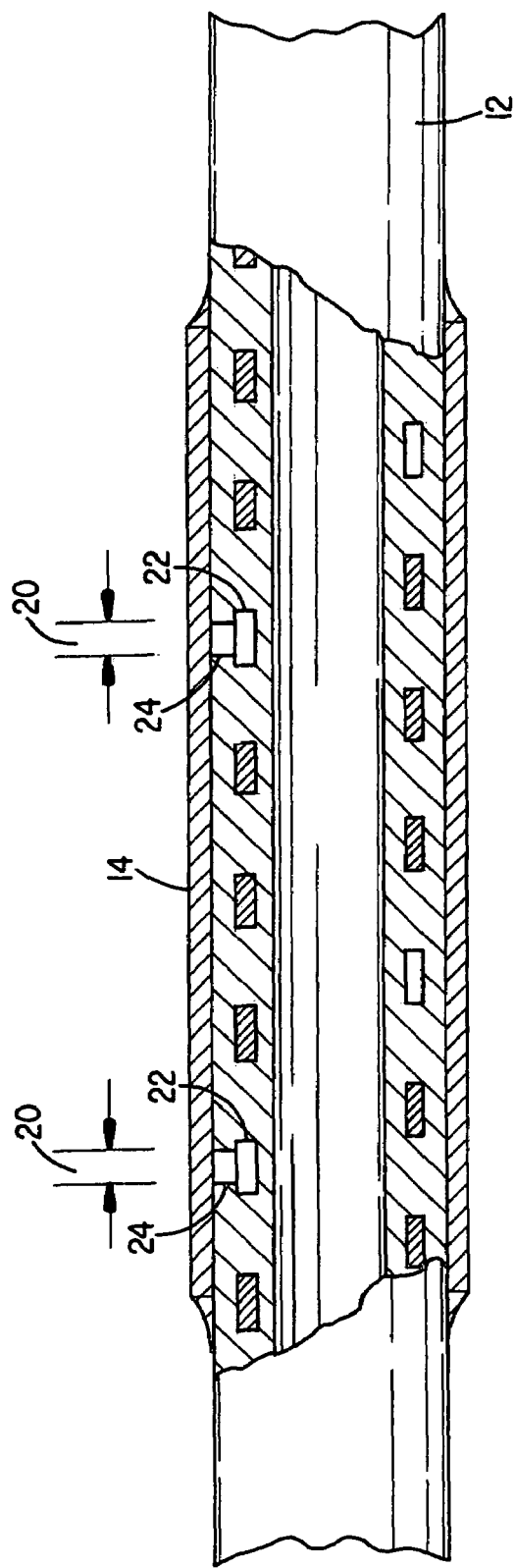
FIG. 2 illustrates a longitudinal cross-sectional view of a of a lead showing an embodiment of the connection between a coiled conductor and a band with a conductive pad.

FIG. 2 illustrates the details of an embodiment of the connection between a conductor 22 and band electrode 14 in accordance with the present invention. Band electrodes are the point of electrical contact between the conductors and the patient. Although discussed in the context of a band electrode, one skilled in the art will recognize that the following description is also applicable to a band connector, a sensor or other electrical element. For exemplary purposes, band electrode 14 and lead body 12 is configured for two welds at a welding region 20. At least one weld is typically utilized. In the particular embodiment, the same conductor is connected to band electrode 14 twice. FIG. 2 illustrates a longitudinal cross-section of a lead body having four spirally wound conductors for exemplary purposes. The lead body is shown with four conductors. The conductors may be visible through the insulating material when the insulating material is translucent.

Figure 3:
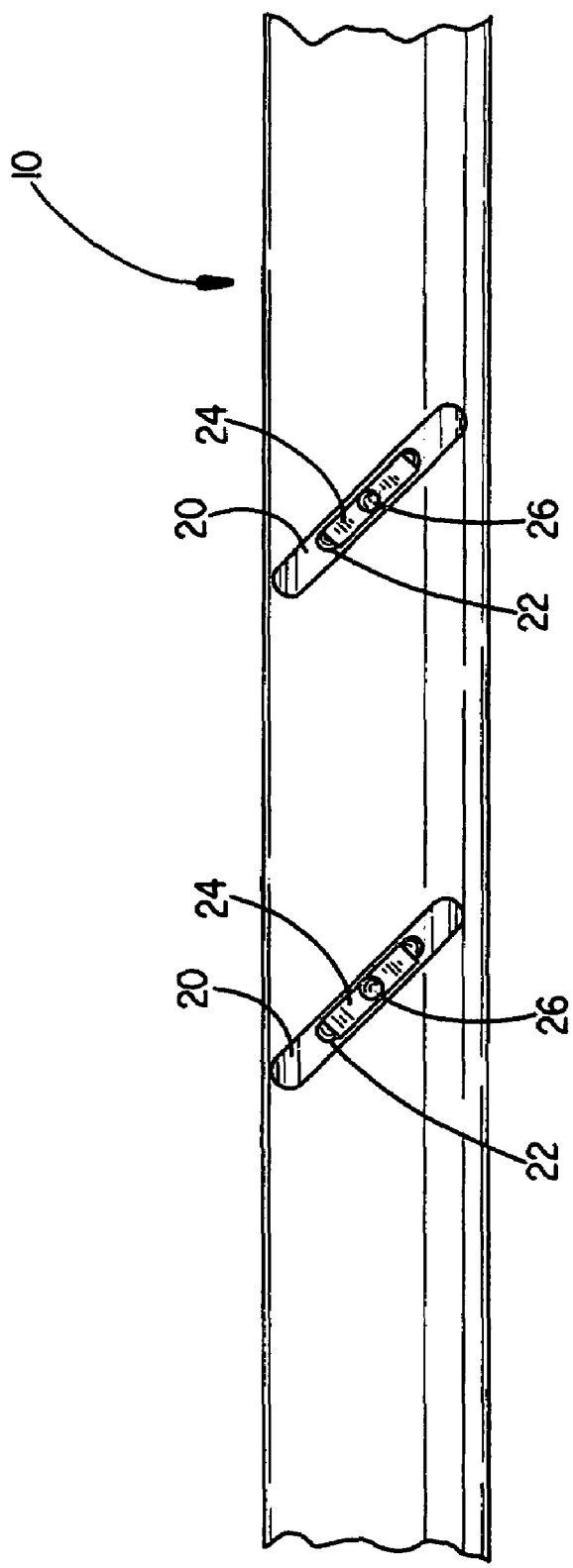
FIG. 3 illustrates a top view of a lead, as shown in FIG. 2, without the band.

FIG. 3 illustrates a top view of a lead body having the insulating material removed to form welding region 20 by exposing conductor 22. As shown in FIG. 3, the welding region 20 is formed obliquely relative to the lead body. Welding region 20 provides access to conductor(s) 22 for electrically connecting band electrode 14 to conductor 22. Welding region 20 is typically formed by removing the insulating material from lead body 10. The insulating material is removed to expose small sections of the individual conductors 22 without breaching an inner lumen, if present. Typically, an excimer laser is used to remove the insulating material. When the insulator is removed by laser, welding region 20 may be in the form of a groove in the insulator. Although, welding regions may take a variety of forms and orientations that expose a sufficient surface area of conductor 22 to form an electrical connection with a conductive pad, discussed below. When in the form of a groove, welding region 20 is typically formed such that the groove runs parallel to conductor 22. Regardless of the form of welding region 20, enough insulating material is removed to expose sufficient surface area of conductor 22 for securing a conductive pad or elongated conductive element to the conductor.

Referring to FIGS. 2 and 3, a conductive pad 24 is positioned within welding region 20 during manufacture to facilitate the electrical connection of band electrode 14 and conductor 22. A weld 26 is typically used to secure the conductive pad 24 in electrical contact with conductor 22. Alternatively, conductive pad 24 may be secured using an adhesive. Conductive pad 22 may be composed of any of a variety of conductive materials that can be welded or secured with adhesives. The metal may be stainless steel, MP35N, Pt-Ir, platinum, silver, gold, copper, vanadium or other metal that will be recognized by one skilled in the art upon review of this disclosure. Conductive pad 24 is positioned within welding region 20 so that conductive pad 24 is in electrical contact with conductor 22. Typically, conductive pad 24 is welded to the conductor prior to placing band electrode 14 over the welding regions and conductive pads 24. A pulsed Neodymium:yttrium-arsenic-garnet (YAG) laser may be used to weld conductive pad 24 to conductor 22. FIG. 2 shows a side view of a cross-section of two grooves 20 that expose two regions of the same conductor 22. Conductive pads 24 are welded to conductor 22 within grooves 20. Band electrode 14 is placed over lead body 12 of lead 10 and welded to conductive pads 24, thereby securing band electrode 14 to lead body 12 and electrically connecting conductor 22 and band electrode 14. Band electrode 14 may be further secured to lead body 12 by swaging, crimping and/or adhesives. Alternatively, the band electrode may be secured to the lead body by heating the lead body. Heating the lead body stress-relieves the plastic increasing the outside diameter and securing the band electrode over the lead body. In addition, heating the lead body may be used to create a lead having a uniform diameter band and lead body.

Figure 4:
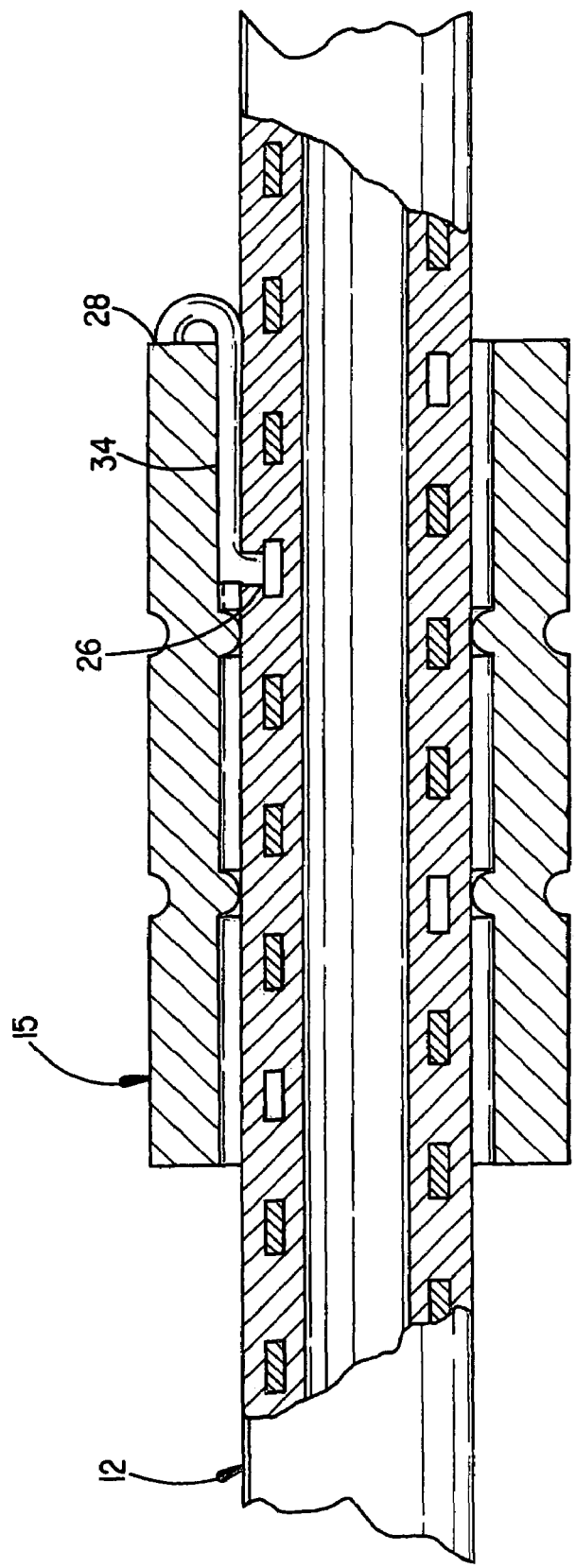
FIG. 4 illustrates a longitudinal cross-sectional view of a lead showing the connection between a coiled conductor and a band with an elongated conductive element.
Figure 5:
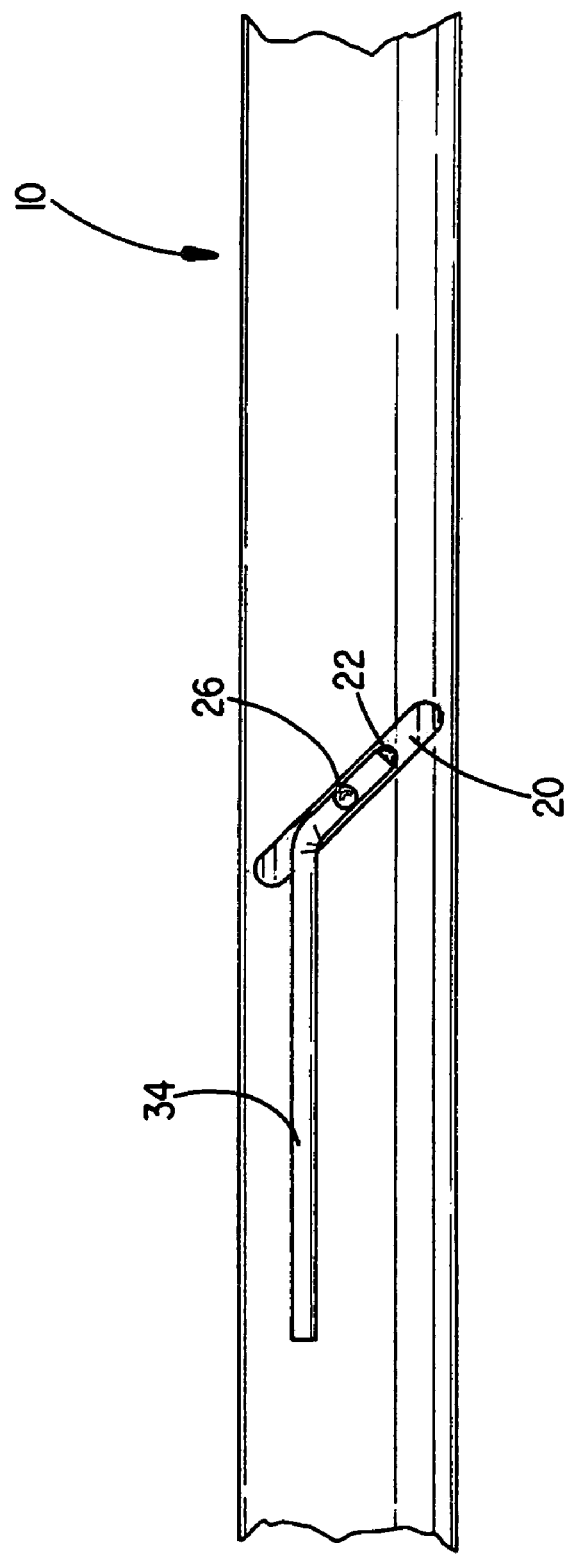
FIG. 5 illustrates a top view of a lead, as shown in FIG. 4, without the band.

FIGS. 4 and 5 illustrate the details of another embodiment of a connection between conductor 22 and a band connector 15 in accordance with the present invention. Band connectors are the point of electrical contact between the medical device using the lead and the conductors within the lead. Although discussed in the context of a band connector, one skilled in the art will recognize that the following description is also applicable to band electrodes, sensors or other electrical elements. An elongated conductive element 34 is used to electrically connect the band to conductor 22. The elongated conductive element may be in the form of a wire, a ribbon wire, or a cable. The metal may be stainless steel, MP35N, Pt-Ir, platinum, silver, gold, copper, vanadium or other metal that will be recognized by one skilled in the art upon review of this disclosure. A distal end of elongated conductive element 34 is electrically connected to band connector 15. Typically, the electrical connection employs a weld 28, although a conductive adhesive or other method of conductively attaching may be used. FIG. 4 shows a longitudinal cross-section of a lead body having four spirally wound conductors. One or more welding regions 20 are formed through the insulating material by removing the insulating material from lead body 10. Typically, the insulating material is removed with a laser. The proximal end of elongated conductive element 34 is positioned within welding region 20 so that the proximal end is in electrical contact with conductor 22. Typically, the proximal end is secured to conductor 22 prior to placing band connector 15 over lead body 12. Again, the proximal end is typically welded although a conductive adhesive or other method of conductively attaching the proximal end may be used. The elongated conductive element 34 and attached proximal end are typically configured to allow band connector 15 to pass over elongated conductive element 34 during assembly. The distal ends of elongated conductive elements 34 may then be electrically connected to band connector 15.

FIGS. 4 and 5 illustrate a single exemplary connection between conductor 22 and band connector 15 by welds 26 and 28. Thus, FIG. 4 shows only one groove 20 exposing conductor 22. The proximal end of elongated conductive element 24 is positioned within groove 20 is welded to conductor 22. Band connector 15 is placed over lead body 12 and welded to elongated conductive element 34, thereby electrically connecting conductor 22 and band connector 15. Band connector 15 may be further secured to lead body 12 by swaging, crimping, adhesives and/or insert molding. In addition, swaging may reduce the outside diameter of lead connector 15 to permit the manufacture of a lead of uniform diameter. Further, lead body 12 may be expanded by heating to create a uniform diameter for lead connector 15.

Figure 6A:
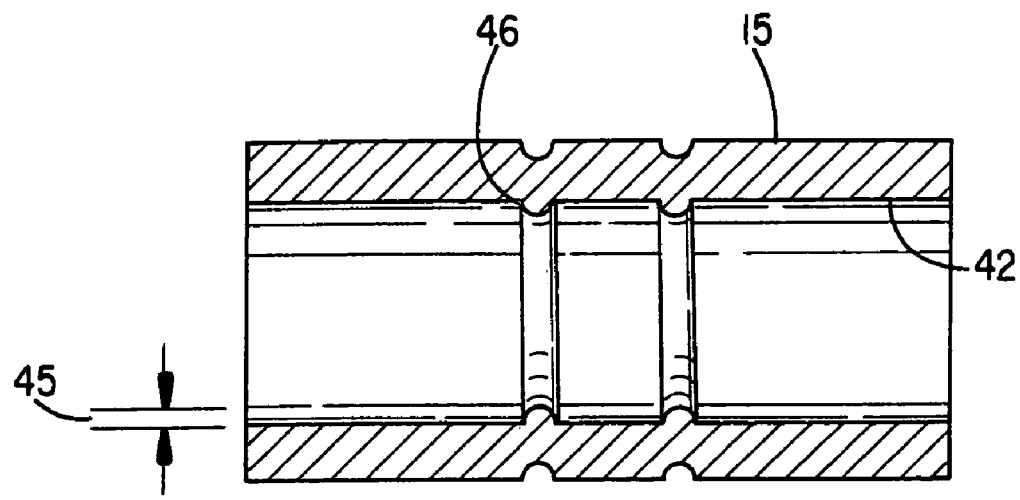
FIG. 6A illustrates a cross-sectional longitudinal view of a band electrode, as shown in FIGS. 4 and 5.
Figure 6B:
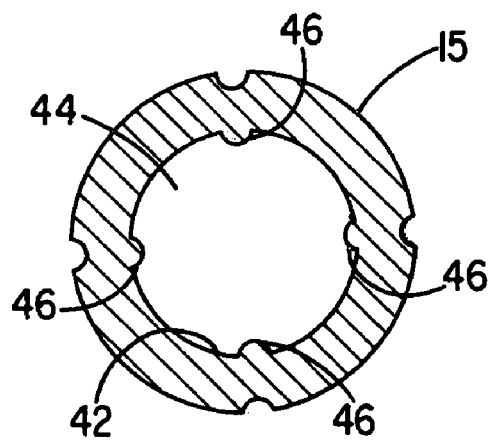
FIG. 6B illustrates and end view of the band electrode, as in FIG. 6A.

FIGS. 6A and 6B illustrate an embodiment of a band which may be used in conjunction with the present invention. Although discussed in the context of a band connector, one skilled in the art will recognize that the following description is also applicable to band electrodes, sensors or other electrical elements. Band connector 15 includes an inner wall 42 defining a lumen 44. At least one projection 46 is formed on the inner wall 42. Projections 46 define a space between inner wall 42 and an outer surface of the lead body during assembly. Projections 46 may be molded on the inner surface; formed by crimping the exterior surface of the band; or added as separate elements secured to the inner surface of the band. Projections 46 have a height 45 which defines the amount of space between the outer surface of the lead body and inner wall 42. Height 45 is generally selected to allow conductive pads 24 and/or conductive elements 34 to pass beneath the inner wall during assembly. Typically, three projections are provided at positions around the circumference of band connector 15 to center band connector 15 over lead body 12 during assembly. Centering band connector 15 so that height 45 is substantially the same around the circumference of the lead body assures clearance of the conductive element during assembly.

The invention claimed is:

1. A medical lead, comprising:
   a lead body having an insulator and multiple conductors, wherein the insulator includes a respective welding region for each of said multiple conductors formed by removal of at least a portion of the insulator, each welding region formed to expose at least a portion of a respective conductor, wherein each welding region is formed obliquely across said lead body and parallel to a respective conductor;
   a respective elongated conductive element, for each welding region, having a distal end and a proximal end, the proximal end electrically connected to the conductor within the corresponding welding region; and
   a respective band welded to the distal end of each elongated conductive element to electrically connect the band to the respective conductor, the band welded to the distal end of the elongated conductive link element outside of the welding region.

2. A medical lead, as in claim 1, wherein each welding region comprises a groove cut in the insulator.

3. A medical lead, as in claim 1, wherein each elongated conductive element is selected from the group consisting of wire, ribbon wire, and cable.

4. A medical lead, as in claim 1, wherein each elongated conductive element is electrically connected to the respective conductor using a method selected from the listing consisting of crimping and conductive adhesives.

5. A medical lead, as in claim 1, wherein each elongated conductive element comprises a material selected from the group consisting of stainless steel, MP35N, platinum, gold, silver, copper, and vanadium.

6. A medical lead, as in claim 1, wherein each band is selected from the group consisting of a band electrode, a band conductor, and a sensor.

7. A medical lead, as in claim 1, wherein each band further comprises a plurality of projections on an inner wall of a lumen, wherein the projections space the inner wall from an outer surface of the lead body.

8. A medical lead, as in claim 7, wherein at least three projections are positioned in the inner wall to center the lead body within the lumen.

* * * * *